(12) United States Patent
Song et al.

(10) Patent No.: US 9,744,508 B2
(45) Date of Patent: Aug. 29, 2017

(54) APPARATUS FOR REVAPORIZING GAS HYDRATE PELLETS

(71) Applicants: Dongguk University Industry-Academic Cooperation Foundation, Seoul (KR); Dongshin Hydraulics Co., Ltd., Busan (KR); Korea Gas Corporation, Seongnam-si, Gyeonggi-do (KR); Sungilturbine Co., Ltd., Busan (KR); Daewoo Engineering & Construction Co., Ltd., Seoul (KR); STX Offshore & Shipbuilding Co., Ltd., Changwon-si, Gyeongsangnam-do (KR)

(72) Inventors: Myung Ho Song, Seoul (KR); Yong Seok Yoon, Seoul (KR); In Kee Jung, Uijeongbu-si (KR); Jung Wook Kim, Seoul (KR); Seung Hee An, Ansan-si (KR); Sang Yup Jang, Ansan-si (KR); Jae Won Lee, Seoul (KR); Sang Min Kim, Busan (KR); Jin Seop Yang, Busan (KR); Ta Kwan Woo, Busan (KR)

(73) Assignees: Dongshin Hydraulics Co., Ltd., Busan (KR); Korea Gas Corporation, Seongnam, Gyeonggi-Do (KR); Sungilturbine Co., Ltd., Busan (KR); Daewoo Engineering & Construction Co., Ltd., Seoul (KR); STX Offshore & Shipbuilding Co., Ltd., Seoul (KR)

( * ) Notice: Subject to any disclaimer, the term of this patent is extended or adjusted under 35 U.S.C. 154(b) by 193 days.

(21) Appl. No.: 14/768,419

(22) PCT Filed: Jun. 27, 2013

(86) PCT No.: PCT/KR2013/005691
§ 371 (c)(1),
(2) Date: Aug. 17, 2015

(87) PCT Pub. No.: WO2014/208791
PCT Pub. Date: Dec. 31, 2014

(65) Prior Publication Data
US 2016/0016135 A1  Jan. 21, 2016

(51) Int. Cl.
*B01J 7/00* (2006.01)
*B01J 3/04* (2006.01)
(Continued)

(52) U.S. Cl.
CPC . *B01J 3/04* (2013.01); *B01J 7/00* (2013.01); *B01J 19/10* (2013.01); *B01J 19/18* (2013.01);
(Continued)

(58) Field of Classification Search
CPC .................................. C10L 3/108; C10L 5/363
See application file for complete search history.

(56) References Cited

U.S. PATENT DOCUMENTS 3,676,091 A * 7/1972 Fraser .................. B08B 9/0556
134/8
2010/0244292 A1* 9/2010 Iwasaki .................. B30B 11/16
264/6
(Continued)

FOREIGN PATENT DOCUMENTS

JP  2006-218367 A  8/2006
JP  2007-187086 A  7/2007
(Continued)

OTHER PUBLICATIONS

International Search Report for PCT/KR2013/005691 dated Mar. 25, 2014.

*Primary Examiner* — Imran Akram
(74) *Attorney, Agent, or Firm* — Locke Lord LLP; Howard M. Gitten

(57) ABSTRACT

The present invention provides an apparatus for regasifying gas hydrate pellets that includes: a cylinder; a piston coupled to an inside of the cylinder and configured to reciprocate up and down; a pellet providing part coupled to an one side of the cylinder in such a way that supply of gas hydrate pellets to the cylinder is adjusted by having one end thereof opened and closed by reciprocation of the piston; a pressure adjusting space having one end thereof coupled to a lower portion of the cylinder; a door formed in the pressure adjusting space and configured to define the pressure adjusting space; a transfer part having one end thereof coupled to the other end of the pressure adjusting space and configured to transfer the gas hydrate pellets; and a regasification part coupled to the other end of the transfer part and having heating water therein to allow regasification of the transferred gas hydrate pellets.

21 Claims, 3 Drawing Sheets

(51) Int. Cl.
*B01J 19/18* (2006.01)
*C07C 9/04* (2006.01)
*B01J 19/10* (2006.01)

(52) U.S. Cl.
CPC ......... *C07C 9/04* (2013.01); *B01J 2219/0869* (2013.01); *B01J 2219/0871* (2013.01); *B01J 2219/0886* (2013.01)

(56) References Cited

U.S. PATENT DOCUMENTS

| | | | |
|---|---|---|---|
| 2010/0325955 A1* | 12/2010 | Watanabe | C10L 3/06 48/78 |
| 2011/0064643 A1* | 3/2011 | Lee | B01J 10/00 423/437.1 |
| 2012/0285083 A1* | 11/2012 | Iwasaki | B30B 11/16 44/596 |
| 2014/0203471 A1* | 7/2014 | Iwabuchi | B30B 9/067 264/115 |

FOREIGN PATENT DOCUMENTS

| | | |
|---|---|---|
| JP | 2009-242494 A | 10/2009 |
| KR | 2013-0016270 A | 2/2013 |
| KR | 2013-0059403 A | 6/2013 |

\* cited by examiner

APPARATUS FOR REVAPORIZING GAS HYDRATE PELLETS

CROSS-REFERENCE TO RELATED APPLICATIONS

This application is the national phase under 35 U.S.C. §371 of PCT International Application No. PCT/KR2013/005691, filed Jun. 27, 2013, the entire contents of the aforementioned application is hereby incorporated herein by reference.

BACKGROUND

1. Technical Field

The present invention relates to an apparatus for regasifying gas hydrate pellets, more specifically to an apparatus for regasifying gas hydrate pellets that can increase the processed amount of regasification by use of a piston-type charging apparatus.

2. Background Art

Natural gas is a clean fossil fuel of which the demand has skyrocketed globally and the resource development has been fiercely competed because it generates significantly smaller quantities of carbon dioxide per fuel mass during the combustion than coal and petroleum.

Natural gas that is produced from gas fields is used as fuel through transportation and storage processes after removing mostly sulfur, carbon dioxide, water and polymer hydrocarbon but methane.

Since the price of natural gas is mostly dependent upon the facility and operation costs of implementing the above processes in addition to the margin and interest, the most economical transportation and storage method is selected, considering various factors such as the size of the gas field and the distance to the consumer. The most typical marine transportation method is the LNG (liquefied natural gas) method, and the compressibility of LNG is about 600 when it is normal condition methane.

Nonetheless, the economic feasibility of the LNG method is restricted due to the cryogenic requirement of LNG, and thus the LNG method is applicable for gas fields larger than a specific scale (i.e., currently at least about 3 trillions of cubic feet).

In order for methane, which is the main component of natural gas, to exist stably as a liquid under atmospheric pressure, the temperature needs to be −162 degrees Celsius or lower. Accordingly, metal materials used in the LNG facility exposed to cryogenic conditions need to include high concentrations of expensive nickel so as to minimize the brittleness. Moreover, due to a great difference in temperature between the inside and the outside during the transportation and storage processes, heat influx causes a large amount of BOG (boil off gas) generation.

In order to achieve economic feasibility of developing relatively small scale gas fields by overcoming these shortcomings and saving production costs of natural gas, GTS (gas to solid) technologies have been widely studied to transport/store natural gas using solid gas hydrate as storage medium. Particularly, in 1990, a Norwegian professor, named Prof. Gudmundsson, presented the self-preservation effect theory of hydrate to motivate many industrialized nations, such as Japan, to develop key technologies required for realizing commercial GTS methods.

Natural gas hydrate (NGH), which is a crystalline mixture in which natural gas molecules are encapsulated within solid state lattices of hydrogen-bonding water molecules, has an external shape that is similar to ice and maintains its solid state stably if a pressure that is higher than a certain value is applied at a given temperature. In order for methane hydrate to stably exist thermodynamically under atmospheric pressure, the temperatures needs to be −80 degrees Celsius or lower, but the self-preservation effect of delaying the decomposition of hydrate for several weeks is discovered when ice film is formed on the surface of a hydrate particle at temperatures of about −20 degrees Celsius.

The gas compressibility of NGH is about 170 (that is, about 170 cc of normal condition natural gas is stored in 1 cc of hydrate), which is more disadvantageous than LNG, but the temperature condition for transportation and storage of NGH is more advantageous. Accordingly, it has been theoretically verified that the GTS method using NGH is an economically alternative option of the LNG method for small-to-medium scale gas fields.

The elemental technologies constituting the GTS method include the NGHP (natural gas hydrate pellet) production technology, which transforms natural gas to the pellet type of hydrate before transporting/storing natural gas, and the regasification technology, which recovers natural gas by decomposing the NGH afterwards.

The conventional regasification apparatuses induce decomposition of the NGHP charged inside a storage tank, which is also used for transportation, by supplying hot water through a lower portion of the tank at a location of consumption and discharge decomposed water and cooled feedwater to an outside to recover cracked gas.

However, with this method, it is not possible to produce a large amount of high-pressure gas continuously and to use the residual cracked gas remaining in the tank.

Moreover, while the conventional continuous regasification technology has the basic concept of injecting the NGHP into a regasification reactor heated by hot water and recovering the produced high-pressure gas from the decomposed water, it lacks specific details on how to make a practical regasification apparatus.

The related art is disclosed in Korean Patent Publication No. 2009-0124967 (PROCESS AND APPARATUS FOR PRODUCING THERMOPLASTIC RESIN PELLETS; laid open on Dec. 3, 2009).

SUMMARY

An embodiment of the present invention provides an apparatus for regasifying gas hydrate pellets that can increase the processed amount of regasification of gas hydrate by use of a piston-type charging apparatus.

An embodiment of the present invention provides an apparatus for regasifying gas hydrate pellets that includes: a cylinder; a piston coupled to an inside of the cylinder and configured to reciprocate up and down; a pellet providing part coupled to an one side of the cylinder in such a way that supply of gas hydrate pellets to the cylinder is adjusted by having one end thereof opened and closed by reciprocation of the piston; a pressure adjusting space having one end thereof coupled to a lower portion of the cylinder, a door formed in the pressure adjusting space and configured to define the pressure adjusting space; a transfer part having one end thereof coupled to the other end of the pressure adjusting space and configured to transfer the gas hydrate pellets; and a regasification part coupled to the other end of the transfer part and having heating water therein to allow regasification of the transferred gas hydrate pellets.

The piston may include: a piston head; a body coupled to the piston head and allowing the piston head to reciprocate up and down by receiving a driving force from an outside; and a housing formed to environ the piston head and detachably coupled with the piston head.

The piston head and the housing may be magnetically coupled to each other.

The piston head may be inserted into the pressure adjusting space and configured to close up the pressure adjusting space.

The apparatus for regasifying gas hydrate pellets may further include: a gas supply line formed between the pressure adjusting space and the regasification part and configured to supply gas of the regasification part to the pressure adjusting space; and an adjustment valve formed in the gas supply line and configured to adjust a supply of the gas.

The transfer part may include a transfer screw.

The apparatus for regasifying gas hydrate pellets may further include a water level adjustment tank couple to the regasification part and configured to adjust a level of the heating water.

The apparatus for regasifying gas hydrate pellets may further include a water level adjustment line formed between the regasification part and the water level adjustment tank and configured to provide a moving line of the heating water.

The apparatus for regasifying gas hydrate pellets may further include a drain valve coupled to the water level adjustment tank and configured to adjust a water level of the water level adjustment tank.

The apparatus for regasifying gas hydrate pellets may further include a circulation line formed between the regasification part and the transfer part and configured to circulate the heating water.

The apparatus for regasifying gas hydrate pellets may further include a circulation pump formed in the circulation line and configured to circulate the heating water.

The apparatus for regasifying gas hydrate pellets may further include a heater formed in the circulation line and configured to heat the heating water being circulated.

The apparatus for regasifying gas hydrate pellets may further include a pulverizing part formed between the other end of the transfer part and the regasification part and configured to pulverize the transferred gas hydrate pellets.

The transfer part may be divided into a plurality of sections and further include a pulverizing part formed between the divided sections of the transfer part and configured to pulverize the transferred gas hydrate pellets.

The apparatus for regasifying gas hydrate pellets may further include a mesh net formed in the regasification part and configured to filter the pulverized gas hydrate pellets.

The mesh net may be provided in plurality in a lengthwise direction of the regasification part, and the size of a mesh of the plurality of mesh nets may become increasingly smaller toward an upper portion of the regasification part.

The apparatus for regasifying gas hydrate pellets may further include an agitator formed in the regasification part and configured to stir the heating water with the pulverized gas hydrate pellets.

A pressure inside the regasification part may be between 50 bar and 70 bar.

The apparatus for regasifying gas hydrate pellets may further include an ultrasonic oscillator coupled to the regasification part and configured to provide ultrasonic waves to the regasification part.

With the embodiments of the present invention, it is possible to increase the processed amount of regasification of gas hydrate pellets by use of a piston-type charging apparatus.

DETAILED DESCRIPTION

Figure 1:
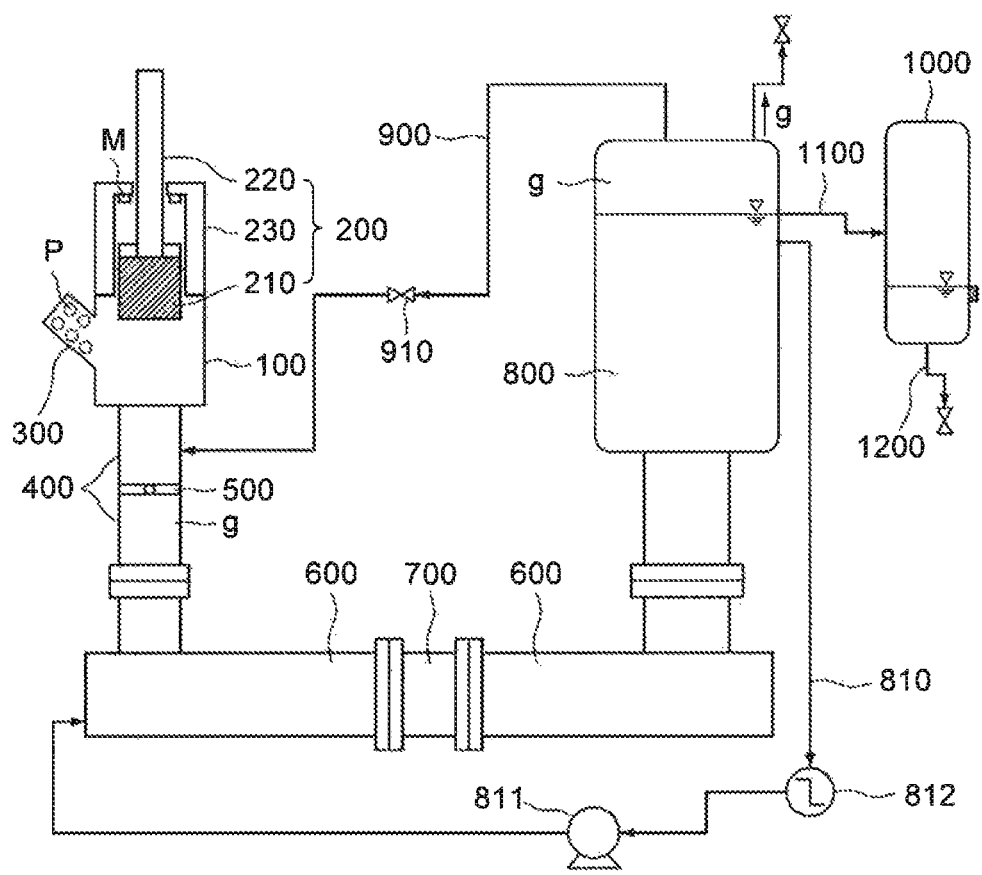
FIG. 1 shows an apparatus for regasifying gas hydrate pellets in accordance with an embodiment of the present invention.

Since there can be a variety of permutations and embodiments of the present invention, a certain embodiment will be illustrated and described with reference to the accompanying drawings. This, however, is by no means to restrict the present invention to a certain embodiment, and shall be construed as including all permutations, equivalents and substitutes covered by the ideas and scope of the present invention. Throughout the description of the present invention, when describing a certain relevant conventional technology is determined to evade the point of the present invention, the pertinent detailed description will be omitted.

The terms used in the description are intended to describe certain embodiments only, and shall by no means restrict the present invention. Unless clearly used otherwise, expressions in a singular form include a meaning of a plural form. In the present description, an expression such as "comprising" or "including" is intended to designate a characteristic, a number, a step, an operation, an element, a part or combinations thereof, and shall not be construed to preclude any presence or possibility of one or more other characteristics, numbers, steps, operations, elements, parts or combinations thereof.

Hereinafter, certain embodiments of an apparatus for regasifying gas hydrate pellets in accordance with the present invention will be described in detail with reference to the accompanying drawings. Identical or corresponding elements will be given the same reference numerals, regardless of the figure number, and any redundant description of the identical or corresponding elements will not be repeated.

Figure 2:
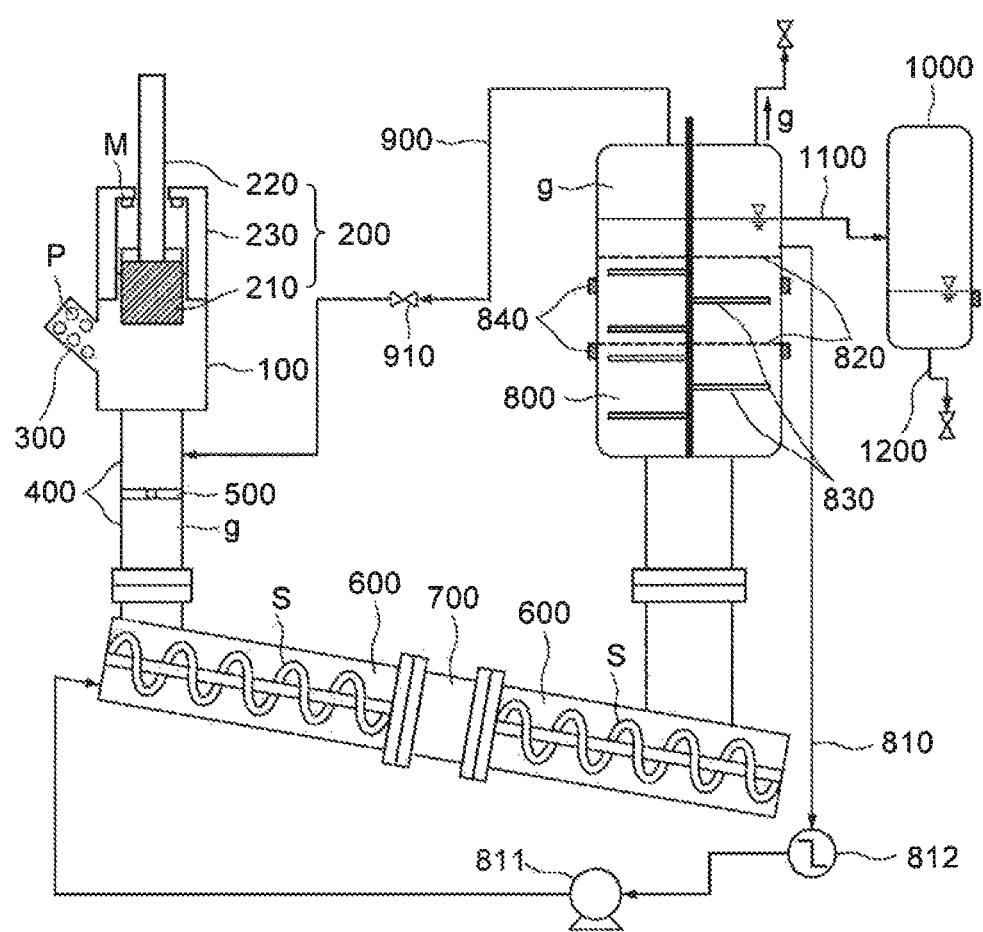
FIG. 2 shows an apparatus for regasifying gas hydrate pellets in accordance with another embodiment of the present invention.

FIG. 1 shows an apparatus for regasifying gas hydrate pellets in accordance with an embodiment of the present invention. FIG. 2 shows an apparatus for regasifying gas hydrate pellets in accordance with another embodiment of the present invention.

Figure 3:
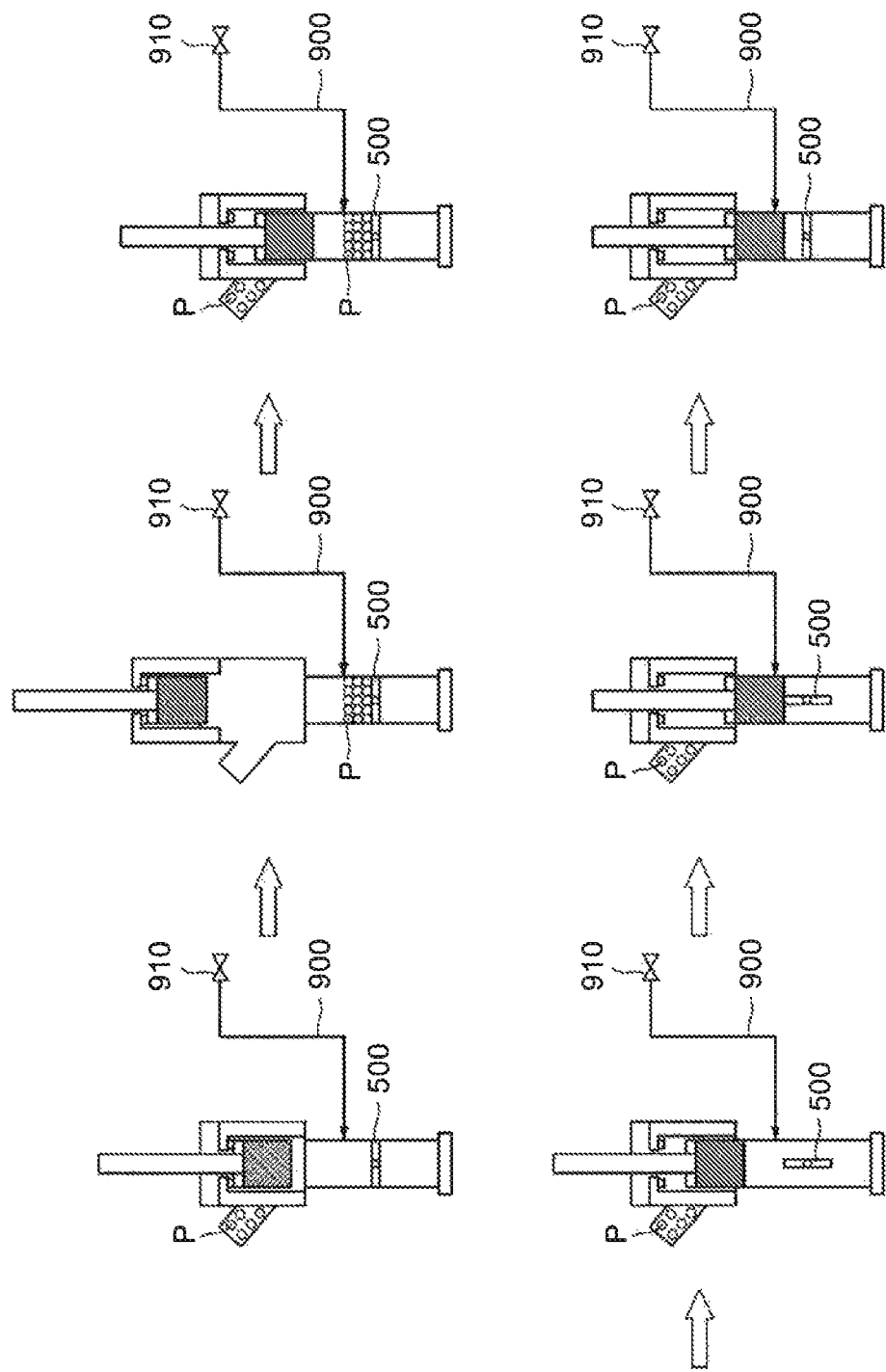
FIG. 3 shows processes for charging gas hydrate pellets with the apparatus for regasifying gas hydrate pellets in accordance with an embodiment of the present invention.

FIG. 3 shows processes for charging gas hydrate pellets with the apparatus for regasifying gas hydrate pellets in accordance with an embodiment of the present invention.

As illustrated in FIG. 1, an apparatus for regasifying gas hydrate pellets in accordance with an embodiment of the present invention includes a cylinder 100, a piston 200, a pellet providing part 300, a pressure adjusting space 400, a door 500, a transfer part 600 and a regasification part 800.

The cylinder 100 is arranged above the pressure adjusting space 400, and the piston 200 is coupled with the cylinder 100 at an inside thereof for an up-down reciprocal motion.

While the piston 200 reciprocates up and down, the pellet providing part 300 coupled to one side of the cylinder 100 may have one end thereof opened and closed.

When the one end of the pellet providing part 300 is closed by a descent of the piston 200, gas hydrate pellets P may be accumulated in the pellet providing part 300 for injection.

When the one end of the pellet proving part 300 is opened by an ascent of the piston 200, the gas hydrate pellets P accumulated in the pellet providing part 300 may be injected to an inside of the cylinder 100.

Here, the pellet providing part 300 may be coupled with the one side of the cylinder at about an angle of 45 degrees.

The pellet providing part 300 may have a level sensor provided at a predetermined upper location thereof to allow a predetermined amount of gas hydrate pellets P to be injected to the inside of the cylinder 100 for each time. That is, while the pellet providing part 300 is closed by the piston 200, the gas hydrate pellets P corresponding to an amount of each injection may be accumulated in the pellet providing part 300.

If the amount of single injection were greater than a maximum amount of gas hydrate pellets P that can be received by the pressure adjusting space 400 closed by the piston 200, the pressure adjusting space 400 and the piston 200 might be damaged, and thus the amount of single injection should be smaller than the maximum amount of gas hydrate pellets P that can be received by the pressure adjusting space 400.

Referring to FIG. 1 to FIG. 3, the piston 200 may include a piston head 210, a body 220 and a housing 230.

The body 220 is coupled to the piston head 210 and is configured to allow the piston head 210 to reciprocate up and down by having a driving force transferred thereto from an outside.

The housing 230 is formed to environ the piston head 210 but may be detachably coupled with the piston head 210.

Here, the piston head 210 and the housing 230 may be coupled by a permanent magnet M.

It is possible that the permanent magnet M is attached either to the piston head 210 or to the housing 230.

Here, it is required that the piston head 210 can be inserted into the pressure adjusting space 400 so as to close up the pressure adjusting space 400.

That is, an outer circumferential surface of the piston head 210 needs to be identical with an inner circumferential surface of the pressure adjusting space 400.

The pressure adjusting space 400 is placed below the cylinder 100 and above the transfer part 600.

The pressure adjusting space 400 has the door 500 installed therein so as to divide the pressure adjusting space 40 into two sections of space.

The door 500 may include a shaft at a center thereof and a revolving door coupled to the shaft.

The revolving door rotates about the shaft such that an internal space of the pressure adjusting space 400 may be divided into two sections of space.

Referring to FIG. 3, the gas hydrate pellets P filled in the pellet providing part 300 are transferred to the transfer part 600 past the pressure adjusting space 400.

The pellet providing part 300 has the gas hydrate pellets P filled therein and has one end thereof closed by the piston 200.

Afterwards, when the piston head 210 of the piston 200 is ascended by a driving force, the housing 230 of the piston 200 is ascended as well, and when the housing 230 reaches an upper portion of the cylinder 100, the one end of the pellet providing part 300 is opened to allow the gas hydrate pellets P filled inside the pellet providing part 300 to be injected into the pressure adjusting space 400 past an internal space of the cylinder 100.

Here, it is required that the pressure adjusting space 400 is already divided into two sections of space by the door 500.

Once the gas hydrate pellets P are completely injected, the piston 200 begins to descend, and the housing 230 of the piston 200 closes the one end of the pellet providing part 300.

Afterwards, the piston 200 continues to descend to close up an upper portion of the pressure adjusting space 400. Here, a thrust is applied to the body 220 to allow the piston head 210 of the piston 200 to descend by breaking off the magnetic coupling with the housing 230, after which the piston head 210 separated from the housing 230 continues to be descended by the thrust.

After the piston head 210 descends to a predetermined height and closes the pressure adjusting space 400 tightly, the piston head 210 stops descending.

The pellets having passed the pressure adjusting space 400 are transferred to the regasification part 800 by the transfer part 600. Here, a high pressure is required for regasification of the gas hydrate pellets P.

That is, the regasification part 800 has high-pressure cracking gas g filled therein.

The regasification part 800 has a constant, high pressure maintained therein, depending on the type and use of the gas, and the transfer part 600 connected with the regasification part 800 also has a similar pressure maintained therein as the regasification part 800.

Moreover, since a lower section of the pressure adjusting space 400 defined by the door 500 is connected with the transfer part 600, the high-pressure cracking gas is also present in the lower section of the pressure adjusting space 400, thereby having a similar pressure therein as the regasification part 800.

When the piston 200 descends and closes the upper portion of the pressure adjusting space 400 defined by the door 500, the pressure in the upper portion of the pressure adjusting space 400 becomes similar to the pressure of the cylinder 100 before the upper portion of the pressure adjusting space 400 is closed, and since the pressure of the cylinder 100 is similar to that of the pellet providing part 300, the pressure in the upper portion of the pressure adjusting space 400 is after all similar to atmospheric pressure.

As the pressure in the upper portion of the pressure adjusting space 400 is similar to atmospheric pressure, and the pressure in a lower portion of the pressure adjusting space 400 is predetermined, a difference of pressure is occurred between the two sections of space within the pressure adjusting space 400 divided by the door 500.

Accordingly, the apparatus for regasifying gas hydrate pellets in accordance with an embodiment of the present invention may further include a gas supply line 900, which is formed in between the pressure adjusting space 400 and the regasification part 800 to supply the high pressure gas of the regasification part 800 to the upper portion of the pressure adjusting space 400 while the upper portion of the pressure adjusting space 400 is closed by the descent of the piston 200.

Moreover, the gas supply line 900 has an adjustment valve 910 formed therein to adjust the supply of the high pressure gas.

That is, after the gas hydrate pellets P are injected to the upper portion of the pressure adjusting space 400 defined by the door 500, the piston 200 may descend and close the upper portion of the pressure adjusting space 400, and the high pressure gas of the regasification part 800 may be flowed into the upper portion of the pressure adjusting space 400 through the gas supply line 900 connect to the upper portion of the pressure adjusting space 400 in order to reduce the difference in pressure between the upper portion of the pressure adjusting space 400 and the lower portion of the pressure adjusting space 400.

Once the difference in pressure between the upper portion of the pressure adjusting space 400 and the regasification part 800 is reduced to a predetermined value, the adjustment valve 910 of the gas supply line 900 is closed.

When the difference in pressure between the upper portion of the pressure adjusting space 400 and the lower portion of the pressure adjusting space 400 becomes similar to the predetermined value, the revolving door of the door 500 rotates, and the gas hydrate pellets P filled in the upper portion of the pressure adjusting space 400 are dropped to the lower portion of the pressure adjusting space 400 by a self-load.

Owing to the gas supply line 900, the gas hydrate pellets P can be transferred to the transfer part 600, without any pressure device or pressure measuring device.

Here, the piston 200 may have a high-pressure thrust transferred thereto so as to push out the gas in the pressure adjusting space 400 with a greater pressure than the pressure in the pressure adjusting space 400.

After the gas hydrate pellets P are injected into the transfer part 600, the high-pressure gas remaining in the pressure adjusting space 400 may be transferred to the transfer part 600 by the descent of the piston head 210 of the piston 200.

Used for power for transferring the high-pressure thrust may be oil pressure.

The gas hydrate pellets P filled in the upper portion of the pressure adjusting space 400 may be transferred to the transfer part 600 past the lower portion of the pressure adjusting space 400 when the door 500 is opened.

Afterwards, the door 500 is closed, and the gas hydrate pellets P for next injection are filled in the pellet providing part 300 while the piston 200 is descended.

Once the amount of gas hydrate pellets P in the pellet providing part 300 reaches the amount of single injection, the piston head 210 begins to ascend, passes through the upper portion of the pressure adjusting space 400, and begins to move together with the housing 230. Accordingly, the housing 230 is ascended by the ascending motion of the piston head 210.

Then, as the one end of the pellet providing part 300 is opened, the gas hydrate pellets P are injected into the cylinder 100, repeating the process described above.

The gas hydrate pellets P transferred to the transfer part 600 are then transferred to the regasification part 800.

The transfer part 600 and the regasification part 800 have heating water filled therein.

Here, the transfer part 600 may include a transfer screw S.

The transfer screw S is coupled and communicated with the lower portion of the pressure adjusting space 400 to transfer the gas hydrate pellets P. The transfer screw S has an inlet provided in one end thereof and an outlet provided in the other end thereof.

A level of the heating water present in the transfer part 600 is dropped below a predetermined height by pressurization of the piston head 210 while the gas hydrate pellets P are injected. Accordingly, there are gas hydrate pellets P that are not immersed in the heating water in an upper portion of the inlet of the transfer screw S, allowing the pellets to be readily injected into the transfer screw S.

The transfer screw S functions to push the gas hydrate pellets P to the regasification part 800.

As illustrated in FIG. 2, the transfer screw S of the apparatus for regasifying gas hydrate pellets in accordance with the present invention may be formed to be gradually lower from the inlet to the outlet so as to facilitate the transfer of the gas hydrate pellets P.

Moreover, a pulverizing part 700 may be interposed between the transfer screw S and the regasification part 800 to pulverize the gas hydrate pellets P being transferred and supply the pulverized gas hydrate pellets P to a lower portion of the regasification part 800.

The pulverizing part 700 is communicated with the outlet placed in the one end of the transfer screw S and pulverizes the gas hydrate pellets transferred thereto. The pellets are partially pulverized while passing through the transfer screw S and further pulverized finely by the pulverizing part 700 before being supplied to the lower portion of the regasification part 800. The gas hydrate pellets P already begin to be decomposed while passing through the transfer screw S and the pulverizing part 700.

The pulverizing part 700, which may be constituted with a rotating blade and a stationary blade that intersect with each other, pulverizes the gas hydrate pellets P to a predetermined particle size or smaller and supplies the pulverized gas hydrate pellets P to the lower portion of the regasification part 800.

The gas hydrate pellets P having passed the pulverizing part 700 and pulverized to the predetermined particle size or smaller have reaction surface areas thereof increased and thus have the decomposition thereof accelerated.

According to another embodiment of the present invention, the pulverizing part 700 may be inserted in the transfer part 600 that is divided into two sections.

That is, the transfer part 600 may be sectioned into an upstream transfer part and a downstream transfer part according to a direction in which the gas hydrate pellets P are transferred, and the pulverizing part 700 may be placed between the upstream transfer part and the downstream transfer part to facilitate the pulverization and transfer of the gas hydrate pellets P.

The regasification part 800 has the heating water therein. As the pulverized gas hydrate pellets P are injected from the lower portion of the regasification part 800 filled with the heating water, the pulverized gas hydrate pellets P are immersed in the heating water while moving from a lower portion to an upper portion of the heating water, improving a heat transfer required for decomposition.

The pulverized gas hydrate pellets P move from the lower portion to an upper portion of the regasification part 800 due to buoyancy and a movement of the heating water caused by a circulation of the heating water.

The regasification part 800 may have a high pressure state maintained therein in order to produce high-pressure gas directly through the regasification part 800.

For example, the regasification part 800 may have an internal pressure thereof at 50 bar to 70 bar. Accordingly, the apparatus for regasifying gas hydrate pellets in accordance with the present embodiment may be installed in a gas turbine requiring high-pressure gas or in a gas supply facility for supplying residential city gas.

It shall be appreciated that the scope of the present invention is not limited to the internal pressure of the regasification part at 50 bar to 70 bar and may be configured variously depending on the type and use of the cracking gas.

As the regasification part 800 maintains the high-pressure state, the pulverizing part 700, the transfer screw S and the transfer part 600, which are communicated with the regasification part 800, also maintain the same high-pressure state as the regasification part 800.

As illustrated in FIG. 2, the regasification part 800 may have a mesh net 820 formed therein that is placed below the level of the heating water and is configured to filter the pulverized gas hydrate pellets P. Moreover, the mesh net 820 may be provided in plurality, depending on a height of the regasification part 800, and the size of the mesh of the plurality of mesh nets 820 may become increasingly smaller toward an upper portion.

Accordingly, an upward moving speed of the pulverized gas hydrate pellets P that have smaller particle sizes with the progress of decomposition may be controlled, and the pulverized gas hydrate pellets P are evenly distributed within the regasification part 800. As a result, an increased contact of the pulverized gas hydrate pellets P with the heating water is provided, and a path through which the cracking gas generated by the decomposition rises after passing through the heating water is secured, thereby increasing the efficiency of decomposition.

Moreover, the regasification part 800 may have an agitator 830 formed therein for stirring the heating water with the pulverized gas hydrate pellets P, in order to facilitate the heat transfer of the pulverized gas hydrate pellets P and the heating water and to separate the generated cracking gas from surfaces of the gas hydrate pellets P more efficiently.

The agitator 830 may be constituted with a shaft arranged in a lengthwise direction of the regasification part 800 and a plurality of moving vanes coupled to the shaft.

Moreover, the regasification part 800 may have an ultrasonic oscillator 840 attached to a surface thereof. The ultrasonic oscillator 840 may be attached to an external surface or an internal surface of the regasification part 800.

It is illustrated in FIG. 2 that a plurality of ultrasonic oscillators 840 are attached to the external surface of the regasification part 800. Ultrasonic waves generated by the ultrasonic oscillator 840 are transferred using the heating water as a medium to facilitate the decomposition of the pulverized gas hydrate pellets P.

The heating water of the regasification part 800 may be discharged at the upper portion of the regasification part 800, and by heating the discharged heating water and flowing the heating water into the transfer part 600, the heating water may be continually circulated in the transfer part 600, the pulverizing part 700 and the regasification part 800.

Provided for this may be a circulation line 810, which is configured to retrieve the heating water at the upper portion of the regasification part 800 and supply the heating water to the transfer part 600, a circulation pump 811, which is interposed in the circulation line 810 and configured to circulate the retrieved heating water, and a heater 812, which is interposed in the circulation line 810 and configured to heat the retrieved heating water.

The heating water retrieved at the upper portion of the regasification part 800 through the circulation line 810 is heated by the heater 812 and then supplied back to the transfer part 600 through the circulation pump 811.

The quantity of heat supplied by the heater 812 may be controlled so as to maintain the heating water at a predetermined temperature.

Meanwhile, with the progress of decomposition in the regasification part 800, moisture contained in the gas hydrate pellets P is decomposed, and thus the heating water in the regasification part 800 is increased.

Accordingly, the apparatus for regasifying gas hydrate pellets in accordance with the present embodiment may further include a water level adjustment tank 1000, which may maintain the level of the heating water in the regasification part 800 by discharging the increase heating water.

The water level adjustment tank 1000 may be coupled to the regasification part 800 to adjust the level of the heating water.

Here, a water level adjustment line 1000 may be formed between the regasification part 800 and the water level adjustment tank 1000 to provide an over flow type of heating water discharge function.

The water level adjustment tank 1000 may have a drain valve 1200 coupled to a bottom thereof to keep the heating water in the water level adjustment tank 1000 from rising above a predetermined water level.

That is, when the water level of the water level adjustment tank 1000 becomes higher than the predetermined water level, the drain valve 1200 is opened to discharge the heating water in the water level adjustment tank 1000 to an outside.

Here, the water level adjustment tank 1000 may also have a level sensor installed therein in order to measure the level of the heating water.

Although certain embodiments of the present invention have been described above, it shall be appreciated that there can be a variety of permutations and modifications of the present invention by those who are ordinarily skilled in the art to which the present invention pertains without departing from the technical ideas and scope of the present invention, which shall be defined by the appended claims. It shall be also appreciated that a large number of other embodiments than the above-described embodiments are included in the claims of the present invention.

What is claimed is:

1. An apparatus for regasifying gas hydrate pellets, comprising:
    a cylinder;
    a piston coupled to an inside of the cylinder and configured to reciprocate up and down;
    a pellet providing part housing the gas hydrate pellets, coupled to an one side of the cylinder in such a way that supply of gas hydrate pellets to the cylinder is adjusted by having one end thereof opened and closed by reciprocation of the piston;
    a pressure adjusting space having one end thereof coupled to a lower portion of the cylinder;
    a door formed in the pressure adjusting space and configured to define the pressure adjusting space;
    a transfer part having one end thereof coupled to the other end of the pressure adjusting space and configured to transfer the gas hydrate pellets; and
    a regasification part coupled to the other end of the transfer part and having heating water therein to allow regasification of the transferred gas hydrate pellets.

2. The apparatus of claim 1, wherein the piston comprises:
    a piston head;
    a body coupled to the piston head and allowing the piston head to reciprocate up and down by receiving a driving force from an outside; and
    a housing formed to environ the piston head and detachably coupled with the piston head.

3. The apparatus of claim 2, wherein the piston head and the housing are magnetically coupled to each other.

4. The apparatus of claim 3, wherein the piston head is inserted into the pressure adjusting space and configured to close up the pressure adjusting space.

5. The apparatus of claim 1, further comprising:
    a gas supply line formed between the pressure adjusting space and the regasification part and configured to supply gas of the regasification part to the pressure adjusting space; and an adjustment valve formed in the gas supply line and configured to adjust a supply of the gas.

6. The apparatus of claim 1, wherein the transfer part comprises a transfer screw.

7. The apparatus of claim 1, further comprising a water level adjustment tank couple to the regasification part and configured to adjust a level of the heating water.

8. The apparatus of claim 7, further comprising a water level adjustment line formed between the regasification part and the water level adjustment tank and configured to provide a moving line of the heating water.

9. The apparatus of claim 8, further comprising a drain valve coupled to the water level adjustment tank and configured to adjust a water level of the water level adjustment tank.

10. The apparatus of claim 1, further comprising a circulation line formed between the regasification part and the transfer part and configured to circulate the heating water.

11. The apparatus of claim 10, further comprising a circulation pump formed in the circulation line and configured to circulate the heating water.

12. The apparatus of claim 11, further comprising a heater formed in the circulation line and configured to heat the heating water being circulated.

13. The apparatus of claim 1, further comprising a pulverizing part formed between the other end of the transfer part and the regasification part and configured to pulverize the transferred gas hydrate pellets.

14. The apparatus of claim 13, further comprising a mesh net formed in the regasification part and configured to filter the pulverized gas hydrate pellets.

15. The apparatus of claim 14, wherein the mesh net is provided in plurality in a lengthwise direction of the regasification part and the size of a mesh of the plurality of mesh nets becomes increasingly smaller toward an upper portion of the regasification part.

16. The apparatus of claim 13, further comprising an agitator formed in the regasification part and configured to stir the heating water with the pulverized gas hydrate pellets.

17. The apparatus of claim 1, wherein the transfer part is divided into a plurality of sections and further comprises a pulverizing part formed between the divided sections of the transfer part and configured to pulverize the transferred gas hydrate pellets.

18. The apparatus of claim 17, further comprising a mesh net formed in the regasification part and configured to filter the pulverized gas hydrate pellets.

19. The apparatus of claim 17, further comprising an agitator formed in the regasification part and configured to stir the heating water with the pulverized gas hydrate pellets.

20. The apparatus of claim 1, wherein a pressure inside the regasification part is between 50 bar and 70 bar.

21. The apparatus of claim 1, further comprising an ultrasonic oscillator coupled to the regasification part and configured to provide ultrasonic waves to the regasification part.

* * * * *